(12) United States Patent
Nakamura

(10) Patent No.: US 10,063,850 B2
(45) Date of Patent: Aug. 28, 2018

(54) SURGICAL STEREOSCOPIC OBSERVATION APPARATUS

(71) Applicant: MITAKA KOHKI CO., LTD., Tokyo (JP)

(72) Inventor: Katsuyuki Nakamura, Tokyo (JP)

(73) Assignee: MITAKA KOHKI CO., LTD., Tokyo (JP)

( * ) Notice: Subject to any disclaimer, the term of this patent is extended or adjusted under 35 U.S.C. 154(b) by 189 days.

(21) Appl. No.: 15/172,748

(22) Filed: Jun. 3, 2016

(65) Prior Publication Data
US 2016/0381347 A1 Dec. 29, 2016

(30) Foreign Application Priority Data

Jun. 23, 2015 (JP) .................. 2015-125273
Nov. 11, 2015 (JP) .................. 2015-220893

(51) Int. Cl.
H04N 13/254 (2018.01)
H04N 13/02 (2006.01)
H04N 13/04 (2006.01)
H04N 13/275 (2018.01)
H04N 13/363 (2018.01)
A61B 1/00 (2006.01)
G03B 15/14 (2006.01)
G03B 35/08 (2006.01)

(52) U.S. Cl.
CPC ............ *H04N 13/254* (2018.05); *A61B 1/00* (2013.01); *G03B 15/14* (2013.01); *G03B 35/08* (2013.01); *H04N 13/0253* (2013.01); *H04N 13/0275* (2013.01); *H04N 13/0459* (2013.01); *H04N 13/275* (2018.05); *H04N 13/363* (2018.05)

(58) Field of Classification Search
CPC .......... H04N 13/0253; H04N 13/0275; H04N 13/0459; H04N 13/254; H04N 13/275; H04N 13/363; A61B 1/00; G03B 15/14; G03B 35/08
See application file for complete search history.

(56) References Cited

U.S. PATENT DOCUMENTS 9,254,078 B2 * 2/2016 McDowall ......... A61B 1/00009
2007/0096038 A1 * 5/2007 Tsai ...................... B82Y 15/00
250/458.1
2015/0297311 A1 * 10/2015 Tesar ....................... G06T 7/30
600/411

FOREIGN PATENT DOCUMENTS

JP          11-318936          11/1999

* cited by examiner

Primary Examiner — Christopher S Kelley
Assistant Examiner — Maria Vazquez Colon
(74) Attorney, Agent, or Firm — Greenblum & Bernstein, P.L.C.

(57) ABSTRACT

A surgical stereoscopic observation apparatus defines main optical paths and secondary optical paths that are branched from the main optical paths A and run to a pair of fluorescence imaging elements. The apparatus picks up both visible-light images and fluorescence images, displays the images on an electronic image display unit, and allows an observer to stereoscopically observe the displayed images.

2 Claims, 6 Drawing Sheets

SURGICAL STEREOSCOPIC OBSERVATION APPARATUS

BACKGROUND OF THE INVENTION

1. Field of the Invention

The present invention relates to a surgical stereoscopic observation apparatus.

2. Description of Related Art

A known surgical stereoscopic observation apparatus has a stand, a camera that is movably supported with the stand and photographs a pair of stereoscopically vie-able electronic images having binocular parallax, and a display unit to display the photographed images. The displayed images are stereoscopically observed with the use of a pair of 3D glasses. Instead of displaying the photographed electronic images on the display unit, a technique disclosed in Japanese Unexamined Patent Application Publication H11-318936 (Patent Literature 1) displays the images on a pair of left and right display panels incorporated in a 3D viewer, so that an observer may stereoscopically observe the displayed images through eyepieces of the 3D viewer.

SUMMARY OF THE INVENTION

The related art mentioned above is able to realize 3D observation of images that are taken by the camera with visible light. The related art, however, is unable to realize 3D observation of images that are taken by the camera with light other than visible light, such as fluorescence exciting light such as infrared light.

In consideration of the problem of the related art, the present invention provides a surgical stereoscopic observation apparatus that is capable of realizing stereoscopic observation of not only images taken with visible light but also images such as fluorescence images taken with fluorescence exciting light.

According to a first aspect of the present invention, the surgical stereoscopic observation apparatus includes a camera. The camera includes two main optical paths that are defined to guide a pair of left and right beams through an objective optical system and through a pair of left and right variable power optical systems to a pair of left and right visible-light imaging elements. The camera also includes two secondary optical paths that are branched from the main optical paths by a pair of left and right optical branching units after the variable power optical systems and defined to guide branched beams to a pair of left and right fluorescence imaging elements. The apparatus also includes an electronic image display unit that displays electronic images taken by the camera with visible light and electronic images taken by the camera with fluorescence exciting light.

According to a second aspect of the present invention, the surgical stereoscopic observation apparatus further includes an illuminating unit that is installed inside the camera and selectively and simultaneously emits visible light and fluorescence exciting light.

According to a third aspect of the present invention, the camera incorporates beam emitters that emit two beams in parallel with an optical axis of the objective optical system toward the objective optical system. The two beams from the beam emitters cross each other at a point of focal length of the objective optical system.

According to a fourth aspect of the present invention, the two beams from the beam emitters enter the objective optical system at points that are different from points where the beams for the variable power optical system exit from the objective optical system.

DESCRIPTION OF PREFERRED EMBODIMENTS

Figure 1:
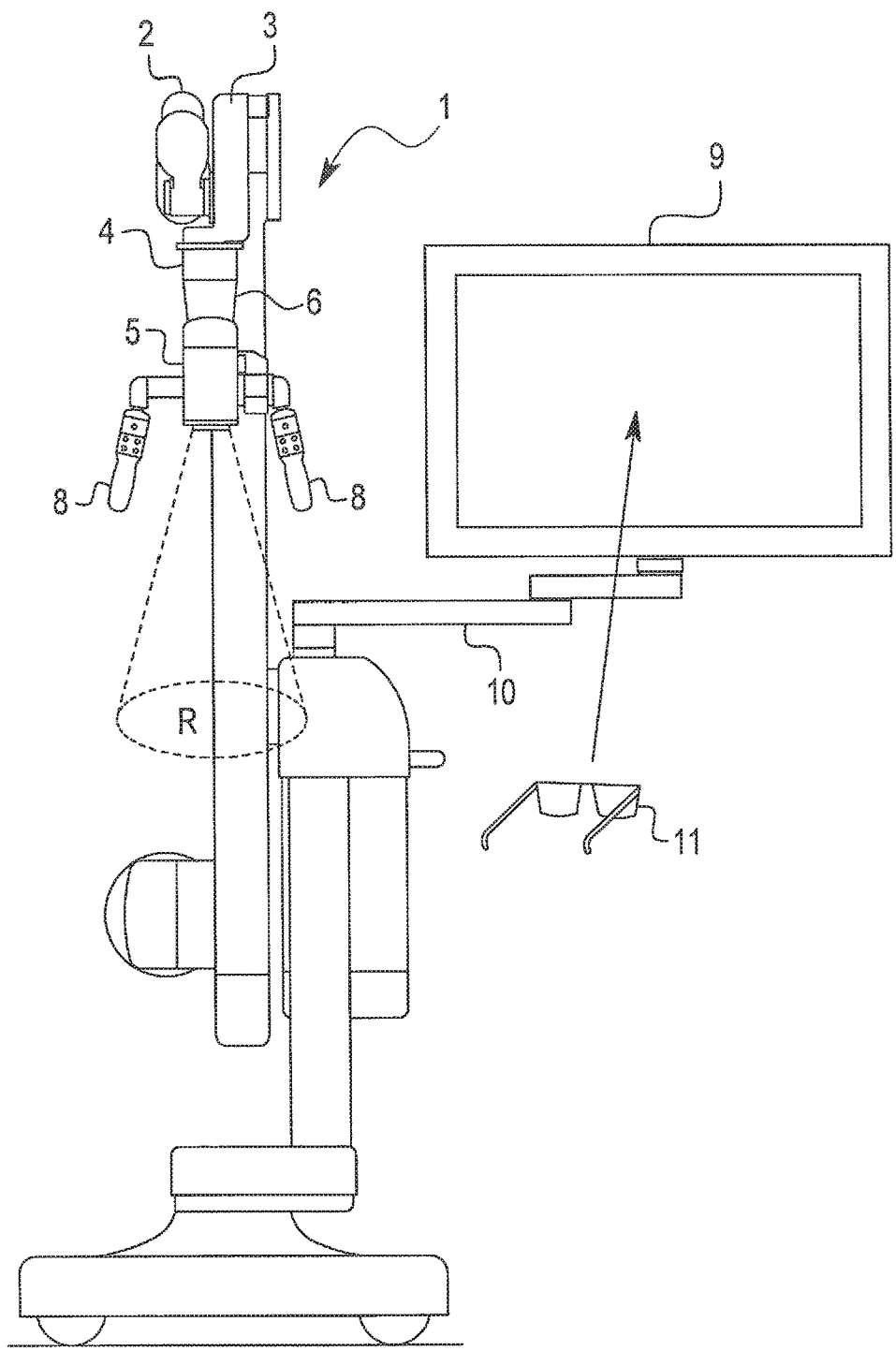
FIG. 1 is a front view illustrating a surgical stereoscopic observation apparatus according to an embodiment of the present invention.
Figure 2:
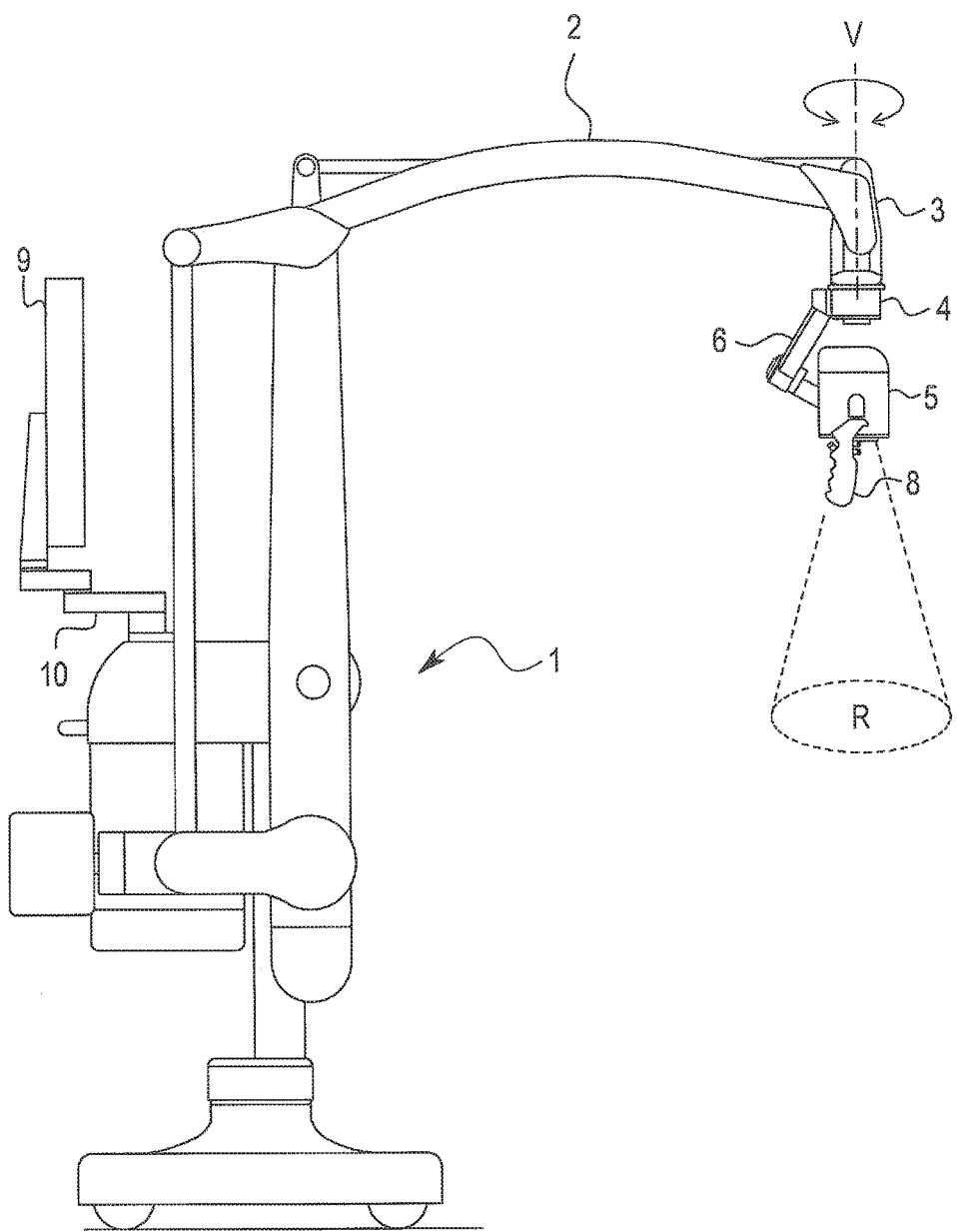
FIG. 2 is a side view illustrating the apparatus.
Figure 3:
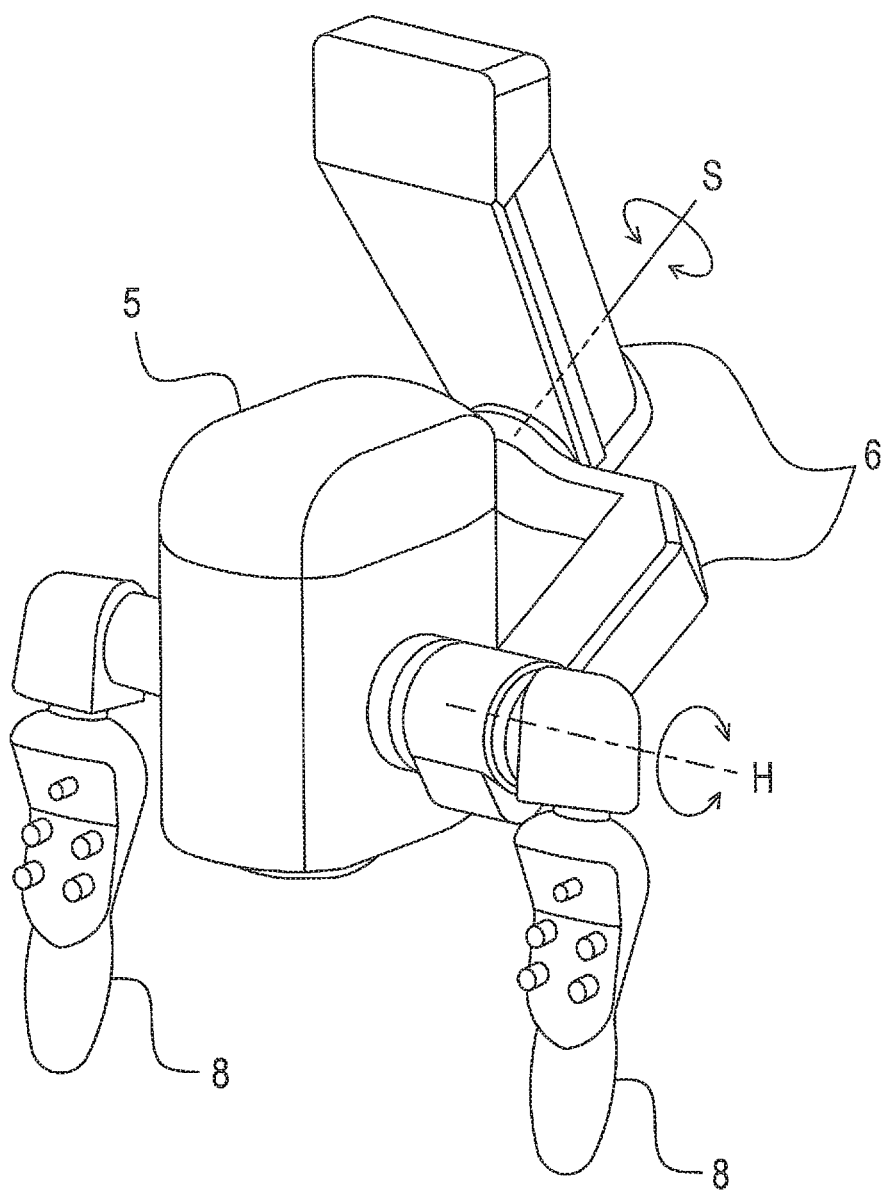
FIG. 3 is a perspective view illustrating a camera installed on the apparatus.
Figure 4:
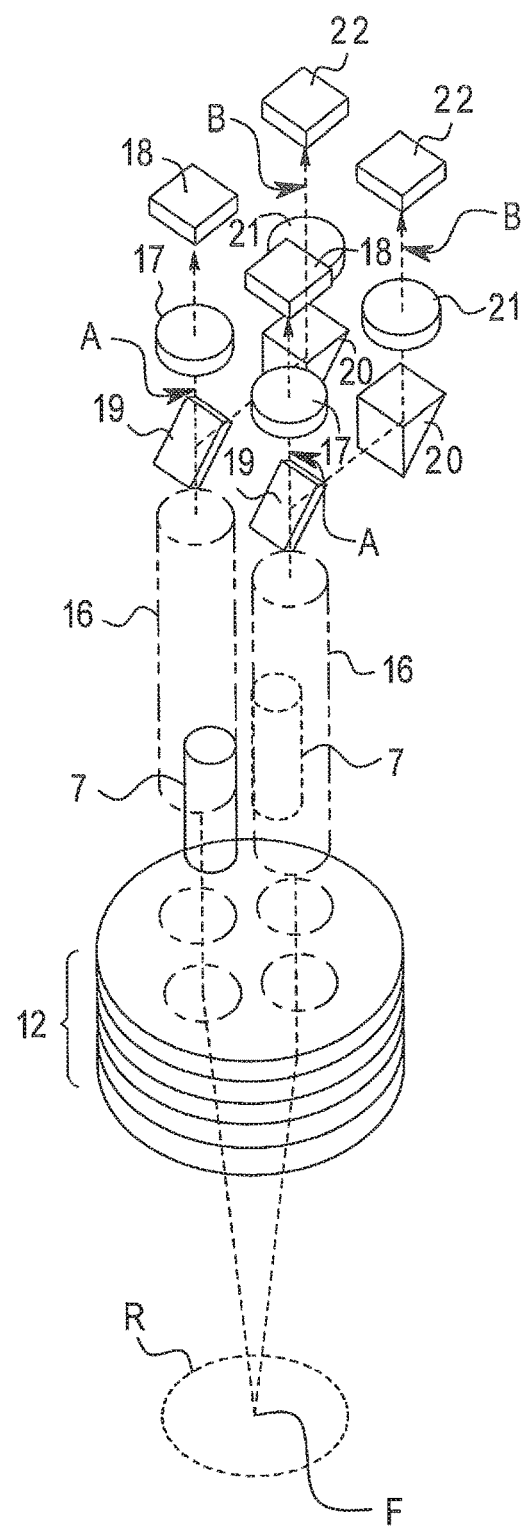
FIG. 4 is a perspective view illustrating an internal structure of the camera.
Figure 5:
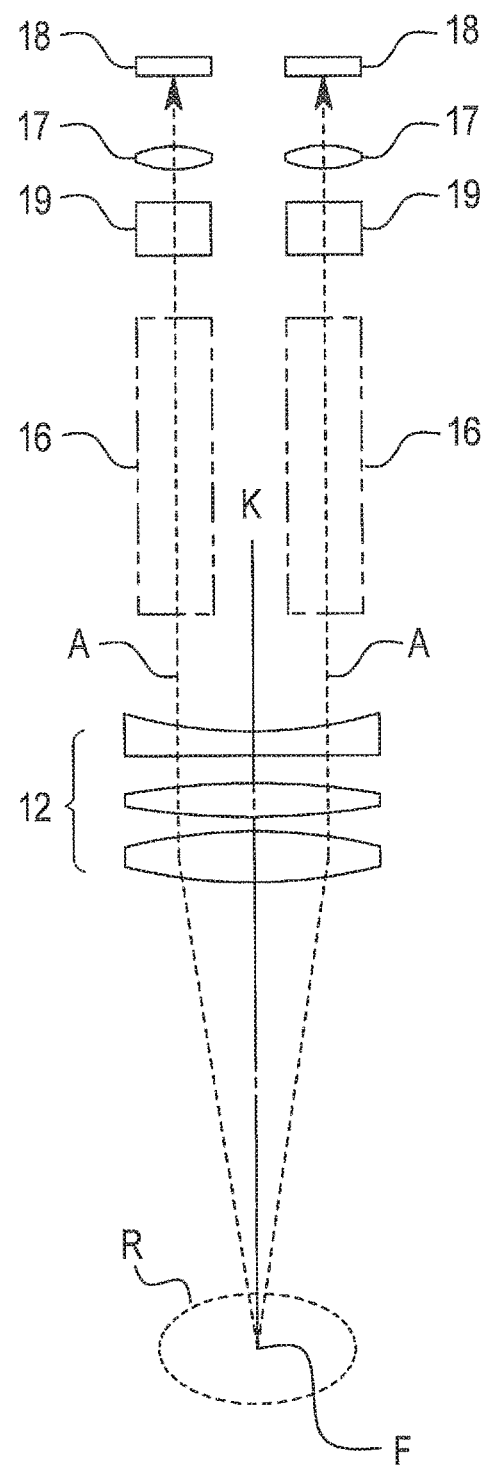
FIG. 5 is a front view illustrating main optical paths defined in the camera.

A surgical stereoscopic observation apparatus according to an embodiment of the present invention will be explained with reference to FIGS. 1 to 6.

The surgical stereoscopic observation apparatus has a stand 1 that has a support arm 2 extending horizontally from the stand 1. The support arm 2 has a parallel linkage structure that keeps a front link 3 of the support arm 2 vertical even if the support arm 2 is moved upward or downward. The front link 3 corresponds to a front vertical side of the parallel linkage structure of the support arm 2 and has a virtual vertical axis V. A lower end of the front link 3 supports a front member 4 that is turnable with respect to the front link 3 around the vertical axis V. The front member 4 has an auxiliary arm 6 that supports a camera 5. The camera 5 is able to change the direction thereof around a horizontal axis H and slant axis S of the auxiliary arm 6. The camera 5 is able to stereoscopically take optical images having binocular parallax of an operative field R.

The camera 5 has a control grip 8 on each side thereof. An operator grasps the grips 8 to move the camera 5 together with the stand 1 to an optional location, or change a spatial position of the camera 5, or orient the camera 5 to an optional direction. The stand 1 has a folding arm 10 that supports an electronic image display unit 9. The display unit 9 may be a liquid-crystal panel or organic light emitting display panel that receives signals from the camera 5, synthesizes the signals in real time to form a pair of electronic images having binocular parallax, and displays the images. An operator or assistant may employ special glasses 11 to stereoscopically observe the images displayed on the display unit 9.

An internal structure of the camera 5 will be explained. The camera 5 has a stereoscopic observation enabling structure. Inside the camera 5, left and right main optical paths A are defined. Arranged at a lower part of the camera 5 is an objective optical system 12. Arranged adjacent to the objective optical system 12 is a douser 13 behind which an illuminating unit 14 is arranged inside the camera 5. The illuminating unit 14 incorporates an LED light source to selectively or simultaneously emit, as illuminating light E, visible light and fluorescence exciting light.

Since the illuminating unit 14 is incorporated in the camera 5, there is no need of connecting an optical cable to the camera 5 to introduce external illuminating light. Such an optical cable is rigid and heavy to hinder the movement of the camera 5 if it is connected to the camera 5. The embodiment has no such a problem because it has no need of connecting such an optical cable to the camera 5.

Arranged above and within the range of the objective optical system 12 is a pair of left and right variable power optical systems 16. The main optical paths A for guiding light flux are defined to pass through the objective optical system 12 and the respective variable power optical systems 16. The main optical paths A run through imaging lenses 17 up to visible-light imaging elements 18. The imaging elements 18 are, for example, CCD area image sensors.

Arranged in each main optical path A between the variable power optical system 16 and the imaging lens 17 is an optical branching unit 19 such as a dichroic mirror. The optical branching unit 19 transmits, along the main optical path A, visible light other than light of fluorescence wavelengths and branches by reflection the light of fluorescence wavelengths to a secondary optical path B. The secondary optical path B is reflected by a prism 20, passes through an imaging lens 21, and reaches a fluorescence imaging element 22.

A pair of beam emitters 7 are arranged inside the camera 5 above the objective optical system 12. The beam emitters 7 are arranged orthogonal to the variable power optical systems 16. Since the beam emitters 7 are arranged out of the main optical paths A in which the variable power optical systems 16 are arranged, the beam emitters 7 never interfere with the variable power optical systems 16. Namely, in the range from the objective optical system 12 to the operative field R, light flux from the beam emitters 7 never interferes with observatory light flux from the operative field R.

Each beam emitter 7 is a compact semiconductor laser emitter to emit a guiding semiconductor laser beam T in parallel with an optical axis K. According to the embodiment, the optical axis K agrees with an optical axis of the objective optical system 12. On the objective optical system 12, the main optical paths and the optical paths of the two guiding beams T are in parallel with the optical axis K and never interfere with each other. The main optical paths A and guiding beams T that are parallel with the optical axis K pass through the objective optical system 12 and a focal point F. More precisely, the guiding beams T pass through the objective optical system 12, converge at a point of focal length of the objective optical system 12, and intersect each other thereat. The guiding beams T are made incident to the objective optical system 12 from the variable power optical system 16 side in parallel with the optical axis K. Accordingly, the guiding beams T always converge at the focal point F without regard to the focal length of the objective optical system 12 that may optionally be changed.

The beam emitters 7 are linked through a controller (not illustrated) to control buttons on the control grips 8. While the control buttons are being pressed, the beam emitters 7 emit the guiding beams T. The control buttons on the control grips 8 are pressed in case of releasing clutches of movable parts of the stand 1, or changing the focal length of the objective optical system 12, or the like.

In this way, the embodiment defines the secondary optical paths B in addition to the main optical paths A, arranges the fluorescence imaging elements 22 in the secondary optical paths B to pick up fluorescence electronic images, and displays the images on the display unit 9. The embodiment is able to display on the display unit 9 a visible-light image and fluorescence image selectively, or one on another, or side by side.

When an operator presses control buttons on the control grips 8 to, for example, move the camera 5, the beam emitters 7 emit the guiding beams T while the buttons are being pressed. When the camera 5 is moved to a required position on an operative field R, the guiding beams T form spots P on the operative field R. The spots P on the operative field R are visible to the naked eye and observable on the display unit 9.

Figure 6:
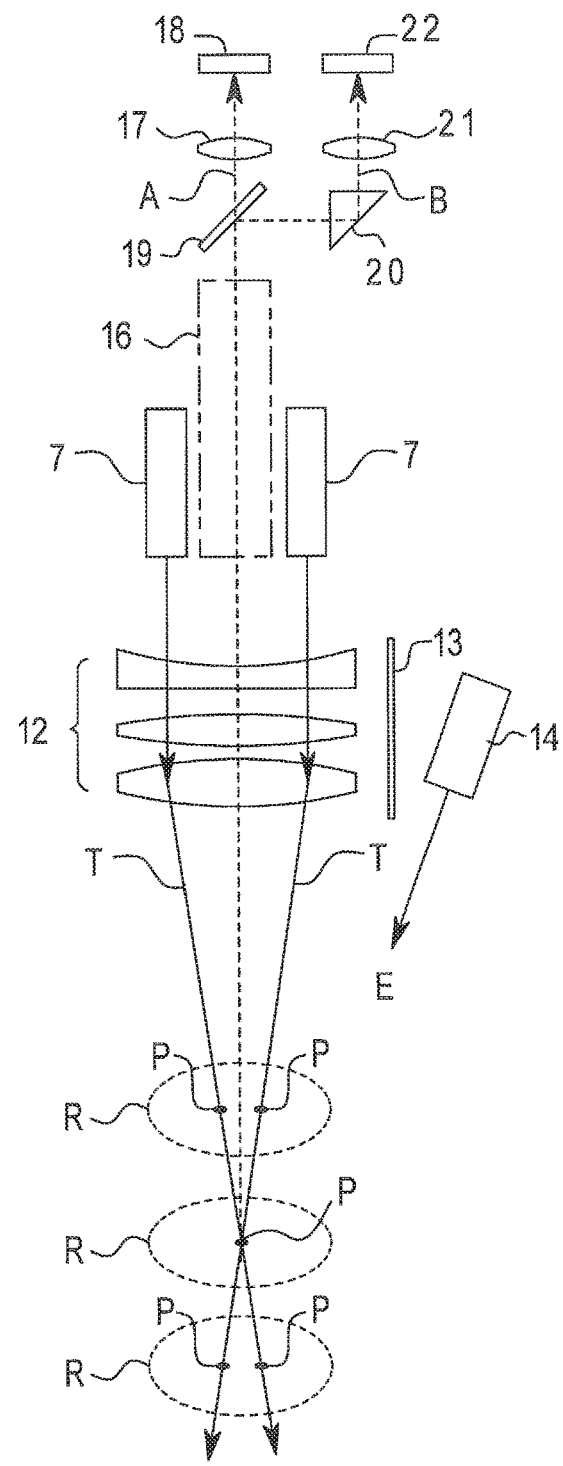
FIG. 6 is a side view illustrating secondary optical paths defined in the camera.

At this time, the spots P converge into a single spot on the operative field R if the focal point F of the objective optical system 12 is correctly positioned on the operative field R as illustrated in FIG. 6. On the other hand, if the focal point F disagrees with the operative field R, the two spots P are discretely observed on the operative field R and a distance between the two spots P is proportional to a deviation from the focal point F.

Whenever moving the stand 1 and camera 5 or changing the focal length of the objective optical system 12 by pressing the control buttons on the control grips 8, the operator is able to instantaneously check to see with the naked eye or on the display unit 9 if the focal point F of the objective optical system 12 is on the operative field R. As a result, the operator is able to speedily and correctly observe the operative field R.

According to the embodiment, images displayed on the display unit 9 are three-dimensionally observed through the special glasses 11. Instead, the images may be displayed on a pair of left and right display panels incorporated in a 3D viewer and stereoscopically observed through eyepieces of the 3D viewer.

According to the first aspect of the present invention, the surgical stereoscopic observation apparatus defines the main optical paths and secondary optical paths. The secondary optical paths are branched from the main optical paths and are guided to the pair of left and right fluorescence imaging elements. With this, the apparatus is able to pick up both visible-light images and fluorescence images and display the images on the display unit, thereby allowing an observer to stereoscopically observe not only the visible-light images but also the fluorescence images.

According to the second aspect of the present invention, the camera of the apparatus incorporates the illuminating unit to selectively and simultaneously emit visible light and fluorescence exciting light. With this, the camera needs no optical cable for introducing external illuminating light into the camera, and therefore, the camera is freely movable without restriction.

According to the third aspect of the present invention, the camera incorporates the beam emitters that emit two beams in parallel with an optical axis of the objective optical system of the camera toward the objective optical system. When a focal point of the objective optical system agrees with an objective operative field, the two beams from the beam emitters converge into a single spot on the operative field. If the focal point disagrees with the operative field, the two beams form two spots on the operative field. With this, an operator is able to instantaneously check to see with the naked eye or on the display unit if the focal point of the objective optical system is on the operative field. If the focal point disagrees with the operative field, the operator vertically moves the camera until the two beams from the beam emitters form a single spot on the operative field. The embodiment thus allows the operator to easily accomplish focusing.

According to the fourth aspect of the present invention, the two beams from the beam emitters enter the objective optical system at points that are different from points where beams for the variable power optical system exit from the objective optical system. With this, the two beams from the beam emitters are able to secure irradiating spots on the objective optical system without interfering with the beams for the variable power optical system.

This patent application claims the benefit of priority under 35 U.S.C. 119(a) to Japanese Patent Applications No. 2015-220893 filed on Nov. 11, 2015 and No. 2015-125273 filed on Jun. 23, 2015 whose disclosed contents are cited herein.

What is claimed is:

1. A surgical stereoscopic observation apparatus comprising:
   a camera including:
   two main optical paths that are defined to guide a pair of left and right beams through an objective optical system and through a pair of left and right variable power optical systems to a pair of left and right visible-light imaging elements;
   two secondary optical paths that are branched from the main optical paths by use of a pair of left and right optical branching units after the variable power optical systems and defined to guide branched beams to a pair of left and right fluorescence imaging elements; and
   an electronic image display unit that displays electronic images taken by the camera with visible light and electronic images taken by the camera with fluorescence exciting light;
   wherein:
   the camera incorporates beam emitters that emit two beams in parallel with an optical axis of the objective optical system toward the objective optical system;
   the two beams from the beam emitters intersect each other at a point of focal length of the objective optical system; and
   the two beams from the beam emitters enter the objective optical system at points that are different from points where the beams that are guided through the variable power optical system exit from the objective optical system.

2. The surgical stereoscopic observation apparatus of claim 1, further comprising:
   an illuminating unit that is installed inside the camera and selectively and simultaneously emits visible light and fluorescence exciting light.

* * * * *